United States Patent [19]

Higuchi

[11] Patent Number: 4,771,004
[45] Date of Patent: Sep. 13, 1988

[54] METHOD FOR IN VITRO DETERMINATION OF TRANSDERMAL ABSORPTION

[75] Inventor: Takeru Higuchi, Lawrence, Kans.

[73] Assignee: IPRX, Inc., Lawrence, Kans.

[21] Appl. No.: 901,732

[22] Filed: Aug. 29, 1986

[51] Int. Cl.$^4$ .................. A61K 35/58; G01N 7/10
[52] U.S. Cl. ................................ 436/5; 424/95;
424/DIG. 7; 73/64.3
[58] Field of Search ............... 73/64.3, 73; 424/2,
424/3, 95, DIG. 7; 210/321.1; 436/178, 5

[56] References Cited

U.S. PATENT DOCUMENTS 3,590,634  7/1971  Pasternak ................. 73/64.3 X
4,594,884  6/1986  Bondi et al. ............. 210/321.2 X Primary Examiner—Barry S. Richman
Assistant Examiner—Jill Johnston
Attorney, Agent, or Firm—Burns, Doane, Swecker & Mathis

[57] ABSTRACT

Provided is a novel barrier membrane and a method using the barrier membrane for testing the transdermal penetration behavior of a bioactive agent. The method employs shed snake skin as the model barrier membrane. In particular, the method comprises the steps of providing a dose of a donor formulation containing the bioactive agent, and a receptor solution, with a barrier membrane of shed snake skin separating the donor formulation and receptor solution. The receptor solution is then serially sampled and assayed in order to determine the concentration of the bioactive agent in the receptor solution. The use of the shed snake skin has been found to provide reproducible and uniform results as a model barrier membrane. As well, the shed snake skin offers the advantages of being readily available and storable for an extended period of time.

16 Claims, 3 Drawing Sheets

METHOD FOR IN VITRO DETERMINATION OF TRANSDERMAL ABSORPTION

CROSS REFERENCE TO RELATED APPLICATIONS

Cross-reference is made to U.S. patent application of Takeru Higuchi for "Methods and Apparatus for Determining the Rate of Movement of a Study Substance through a Membrane", U.S. Pat. No. 4,740,309 filed concurrently herewith.

BACKGROUND OF THE INVENTION

1. Field of the Invention

The present invention relates to an in vitro testing method for studying the penetration behavior of dermal products. More particularly, the present invention relates to the use of a specific model barrier membrane in the study of percutaneous penetration of bioactive agents.

2. Description of the Prior Art

The primary function of the skin of a mammalian organism, including humans, is to protect the body from foreign substances and to control the loss of water, electrolytes and other body constituents. Human skin is mainly composed of three layers. The first layer from the outer surface is the stratum corneum, then the living epidermis and the dermis. In comparison with the last two layers, the stratum corneum has been found to be much less permeable to relatively polar molecules and acts as the primary barrier against the transfer of such molecules across the skin.

The stratum corneum is composed of a mass of dead epidermal cells which in turn consists mainly of keratinized proteins and lipids as well as moisture. Alternate intracellular and intercellular layers comprise the multilamellar structure of the stratum corneum. Its total thickness can vary widely, but averages approximately 10-20 microns. The origin of the intracellular portion is the endogenous material of the living epidermal cell containing mainly keratinized protein. On the other hand, the intercellular portion contains lipids, principally triglycerides, fatty acids, cholesterol and phospholipid, which are derived from epidermal lamellar bodies and nonfibrous protein. Recent work has shown that the barrier function against water molecules is apparently located primarily in the intracellular portion of the stratum corneum.

Due to the barrier properties of the skin, in the development of pharmaceutical products which are intended to be applied to the skin and which provide medications for delivery into the skin, it is highly desirable to have available an in vitro testing method to study the penetration behavior of such dermal products. Indeed, in vitro testing of the availability of bioactive agents from formulations applied to the skin is widely practiced. Due to the lack of a suitable model barrier membrane, however, conventional testing methods have not proven highly satisfactory.

In general, human skin has often been used in in vitro studies since it is obviously the best model barrier membrane to predict the effectiveness of transdermal absorption. Human cadaver skin has generally been used in such instances. Certain animal skins whose properties are thought to be similar to human skin have also been used in many in vitro percutaneous transport studies. The skins of relatively hairless mammals such as the fuzzy rat, the hairless mouse and the baby pig, for example, have been used. The major problem encountered with using cadaver skin or fresh animal skin, however, is the great variability encountered with different samples. Human skin shows particularly large variations in its permeability depending upon site, age, etc. Membrane skin specimens from rats and mice also show similar variations.

Another problem with cadaver skin membrane and fresh skin samples from animals is that they undergo rapid deterioration, sometimes over the period of the test itself, which may last several days. Such problems with decomposition require that the cadaver skin be used within forty-eight hours. Another serious problem is that various substances are released from such fresh tissues, e.g., lipids, which substances interfere with direct analysis of the chemical substance being followed, e.g., by UV spectrophotometric analysis.

Artificial membranes have also been used for in vitro penetration studies because of their uniformity and hydrophobic character, which resembles the stratum corneum of human skin. Their suitability has been found to be less than satisfactory, however, particularly when used with formulations containing dermal enhancers.

Thus, there is a need for a model barrier membrane which closely matches the permeability of the human stratum corneum, but which is also readily available and provides uniform results. The use of such a membrane in in vitro transdermal absorption testing would greatly enhance the test results and ones ability to run the tests.

Accordingly, there is provided by the present invention a novel method for in vitro testing the ability of formulations to deliver bioactive agents across skin.

Another object of the present invention is to provide such a test method which employs a novel barrier or model membrane.

Still another object of the present invention is to provide such a test method which employs a model test membrane comprised of a material which has a permeability profile which closely matches the permeability of the human stratum corneum.

Yet another object of the present invention is to provide such a novel test method which uses a model test membrane comprised of a material which is readily available and provides uniform results.

Another object of the present invention is to provide such a test method which uses a model test membrane comprised of a material which can be stored for extended periods of time.

These and other objects, as well as the scope, nature and utilization of the invention, will be apparent to those skilled in the art from the following description and the appended claims.

SUMMARY OF THE INVENTION

In accordance with the foregoing objectives, the present invention provides a new model barrier membrane for use in in vitro testing of percutaneous absorption, which membrane is comprised of shed snake skin. The method for testing the penetration behavior of a bioactive agent across skin using the snake skin membrane of the present invention comprises providing a dose of a donor formulation containing the bioactive agent to be followed, and a receptor solution. The model barrier membrane of shed snake skin separates the donor formulation and the receptor solution. The receptor solution can then be sampled and assayed, preferably periodically, to determine the concentration of the bioactive agent in the receptor solution. Use of the shed snake skin as the model barrier membrane provides reproducible and uniform results. As well, the shed snake skin offers the advantages of being easily and readily obtainable, and storable, particularly under refrigeration, for an extended period of time.

DETAILED DESCRIPTION OF THE PREFERRED EMBODIMENTS

Figure 1:
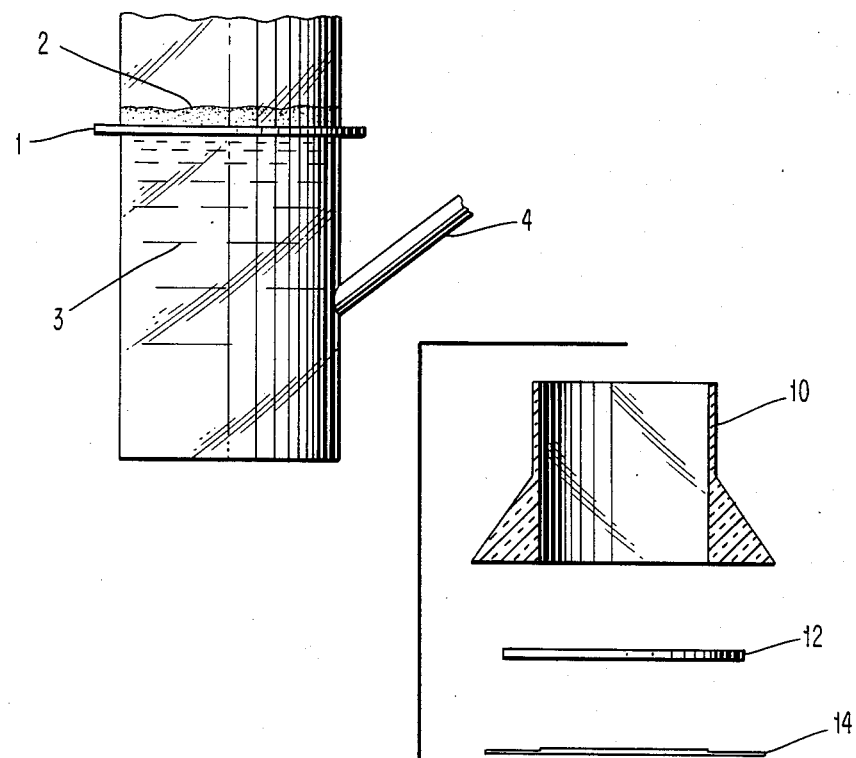
FIG. 1 depicts a diffusion system in which shed snake skin can be used as a model barrier membrane.

The model barrier membrane of the present invention for use in in vitro testing is the skin periodically shed by snakes. It has been surprisingly found that such shed snake skin can serve extremely well as the test membrane in the in vitro determination of transdermal absorption.

The shed snake skin from essentially any species of snake can be used for the purposes of this invention. It is preferred, however, that skin shed by the Black Rat snake be used since it is particularly convenient to obtain. Such species of snake is widely distributed and is easy to raise. For example, each snake, if reasonably well-fed, will shed every two to three months. The shed snake skin from one shedding can generally provide sufficient material for more than twenty experiments with conventional testing cells such as the Franz Diffusion Cell, available from Crown Glass Company, Inc. The snake skin can also be kept for an extended period of time at room temperature or under refrigeration, e.g., at least one week, one month or longer. It is preferred to store the shed skin under refrigeration, however, as the shed snake skin can be kept up to as much as one year under refrigeration.

In using the shed snake skin, a suitable piece of the skin is simply cut to the desired size and shape. The appropriate size and shape, of course, will depend upon the particular apparatus to be used in the testing. The test membrane should be cut to fit properly in the testing apparatus. Preferably, the snake skin is also washed in water and hydrated overnight.

Generally, it is a good idea to also standardize the shed snake skin membranes. This can be easily accomplished by testing the permeability of a sample from each shed skin against a determined standard formulation. An significant variation found in permeability between different shed skin can then be used to normalize results obtained on test formulations using model barrier membranes from the different shed skin.

The use of the shed snake skin as a model barrier membrane in percutaneous absorption studies offers numerous advantages over the use of conventional materials, such as cadaver skin or fresh animal skin. For one, the permeability profile of the shed skin closely matches the permeability of human stratum corneum. Shed snake skin can also be obtained without injury and without killing the animal. There is an increasing concern with all experiments which result in injury and/or death to animals. The use of the snake skin in conventional diffusion cells, such as the Franz Diffusion Cell, also yield permeability results which show variations only as much as one-tenth to one-third as that exhibited by the current practice based on cadaver skin and fresh animal skin. Furthermore, the shed snake skin specimen can be kept for months, particularly under refrigeration, whereas fresh skin samples deteriorate in a few days. Indeed, it has been found that the esterases activity of shed snake skin kept up to 6 months changes very little vis-a-vis newly shed snake skin. This advantage not only reduces the economic cost of the test, but also permits a longer period of study. The snake skin membrane also releases fewer interfering substances when used in a diffusion cell. This permits a much simpler analytical procedure.

The method for testing the penetration behavior of a bioactive agent across skin using the shed snake skin membrane of the present invention can be in accordance with any conventional in vitro method or process known. Generally, however, there is provided a dose of a donor formulation containing the bioactive agent to be followed, and a receptor solution for receiving the bioactive agent. The composition of the formulation can be any ointment, solution or dermal product generally used or proposed to be used by application to skin, with the dose preferably being that approximate to its actual use. The presence of diffusion enhancers in the formulation can aid in the diffusion of the bioactive agent. If desired, the various effects of different enhancers with respect to a particular bioactive agent can also be studied by comparatively testing the different enhancers. The composition of the receptor solution can be any suitable, conventional receptor solution. Generally, however, the receptor solution is such as to simulate the living state in a mammalian organism. For example, the receptor solution can be an isotonic saline solution of a pH of from about 7.2 to 7.4, which is maintained at a temperature of about 32° C. to 37° C.

The model barrier membrane of shed snake skin is then used to separate the donor formulation and the receptor solution. The dose of donor formulation can be applied directly to the membrane as it would in application to the skin of a mammalian organism, such as a human. The receptor solution can then be sampled and assayed by conventional means, e.g., UV spectrophotometric analysis or chromatographic analysis, to ascertain the concentration of the bioactive agent in the receptor solution.

The apparatus and system employing the model barrier membrane of the present invention can be any of those available or used to date in the study of percutaneous absorption. For example, such diffusion cell systems for measurement of percutaneous absorption are available commercially from Crown Glass Co., Inc. of Somerville, N.J. or Vangard International, Inc. of Neptune, N.J. Another imminently suitable diffusion cell system is that disclosed in copending and commonly owned U.S. Pat. No. 4,740,309 filed concurrently herewith, the disclosure of which is hereby expressly incorporated by reference.

One example of a suitable diffusion system in its simplest form is the Franz Diffusion Cell depicted in FIG. 1 of the Drawing. Therein, the shed snake skin can be mounted as the model barrier membrane 1. A thin finite dose of the donor formulation containing the bioactive agent to be followed is applied to the membrane at 2. The receptor solution 3 bathes the membrane 1 from below, and is generally an isotonic saline solution of about pH 7.2 to 7.4. The receptor solution can be maintained at a temperature of about 32° C. to about 37° C. by thermostatically controlled water which is circulated through a jacket surrounding the lower chamber containing the receptor solution. Water circulation can be accomplished by the use of two glass manifolds. A homogeneous distribution of temperature in the receptor solution can be achieved by using a small magnetic stirring bar, drawn by an external magnet mounted on a timing motor. Receptor solution can be removed for the purposes of assaying through arm 4. Additional receptor solution replacing that removed can be added through arm 4 as well.

The following examples are given as specific illustrations of the present invention. It should be understood, however, that the specific details set forth in the examples are merely illustrative and are not meant to be limitative.

In the following examples, the bioactive agent followed was indomethacin. Enhancers employed were N, N-diethyl-n-toleramide (Deet) and 1-dodecylazacycloheptane-2-one (Azone ®).

For the barrier membranes, the molts of adult *Elaphe obsoleta* (black rat snake) were obtained from the Animal Care Unit of the University of Kansas and stored at room temperature for up to 6 months until use. Only the dorsal side of the shed snake skin was used for in vitro penetration studies. No special attention was paid to the age and body weight of the snakes from which the shed skins were obtained. The skins of fuzzy rats, 8 months old and weighing an average of 250 grams, were used as the experimental full thickness rat skin, i.e., living intact dermis and epidermis as well as stratum corneum.

The dose of donor formulation was in the form of an ointment. Several 1% w/w indomethacin ointments each containing a different concentration of Azone ® or Deet were prepared by first dissolving indomethacin in the enhancer. The solution was then mixed with white petrolatum, USP, using a vortex mixer at around 55° C. The ointments were kept in a water bath at $32.0\pm0.1°$ C. for 1 day before use for in vitro penetration studies.

Figure 2:
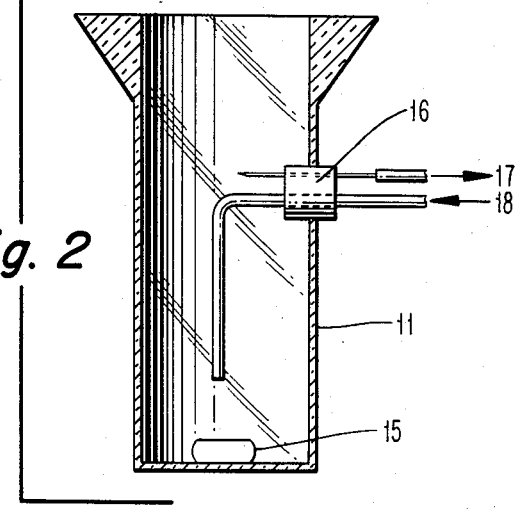
FIG. 2 depicts the diffusion cell used in the experimental runs.

In the in vitro studies, glass diffusion cells as shown in FIG. 2 of the Drawing were used for the shed snake skin membrane. The glass diffusion cells, having a short donor cell 10 and long receptor cell 11, were prepared by using spherical O-ring joints 12. The exposed membrane surface area of the membrane 14 diffusion cell measured 1.8 cm. Before being mounted to the diffusion cell, approximately 25 mg of ointment was carefully applied to the membrane and was spread over the desired area. The membrane was fixed with an O-ring between two sides and fastened tightly with a clamp. The receptor side was filled with approximately 8.5 ml of buffer solution consisting of $1.5\times10^{-1}M$ NaCl, $5.0\times10^{-4}M$ NaH$_2$PO$_4$, and $2.0\times10^{-4}M$ Na$_2$HPO$_4$ adjusted to pH 7.2 with sodium hydroxide. The diffusion cell was immersed vertically in a water bath in which the temperature was maintained at $32.0°\pm0.1°$ C. The receptor cell was stirred constantly with a magnetic stirrer using a magnetic stirring bar 15. To determine the amount of penetrating compounds, 0.2 ml samples were taken at varying time intervals from the receptor solution using a syringe inserted through a septum 16 via 17. An equal amount of fresh buffer was supplied through the septum during sampling via 18.

The rate of drug penetration across the full thickness rat skin was measured using a different type of diffusion cell. This diffusion cell had a surface area of 8 cm$^2$ and approximately 110 mg of ointment was applied to that area. The buffer solution in this receptor cell contained 100 ppm gentamicin sulfate as well as the other constituents described above.

Penetration of indomethacin and the enhancers was followed by HPLC with a CN-RP column. Indomethacin and Deet were analyzed simultaneously, the mobile phase containing 30% v/v acetonitrile -water and 20 mM NH$_4$H$_2$PO$_4$. The mobile phase used in the analysis of Azone ® consisted of 95% v/v acetonitrile -water. Eluents were analyzed at 254 nm for indomethacin and Deet, and at 210 nm for Azone ®.

EXAMPLE 1

The typical penetration behavior of indomethacin from an ointment formulation at 32° C. through shed snake skin was tested with and without Deet as an enhancer. Steady state flow was established in each instance until 20–25% of the applied indomethacin appeared in the receptor cell. These penetration studies were carried out as long as 4 days depending on the rate of penetration. No change was observed in the appearance of the shed snake skins during the studies. For the formulation without any enhancer, no significant amount of indomethacin was observed in the receptor compartment at the end of 4 days of observation. The results of the tests are graphically depicted in FIG. 3 of the Drawing. Least squares values of steady state flux and lag time were calculated from the steady state portion of the curves. These values were used later to quantify the penetration behavior of indomethacin from ointment formulations across the shed snake skin.

Figure 3:
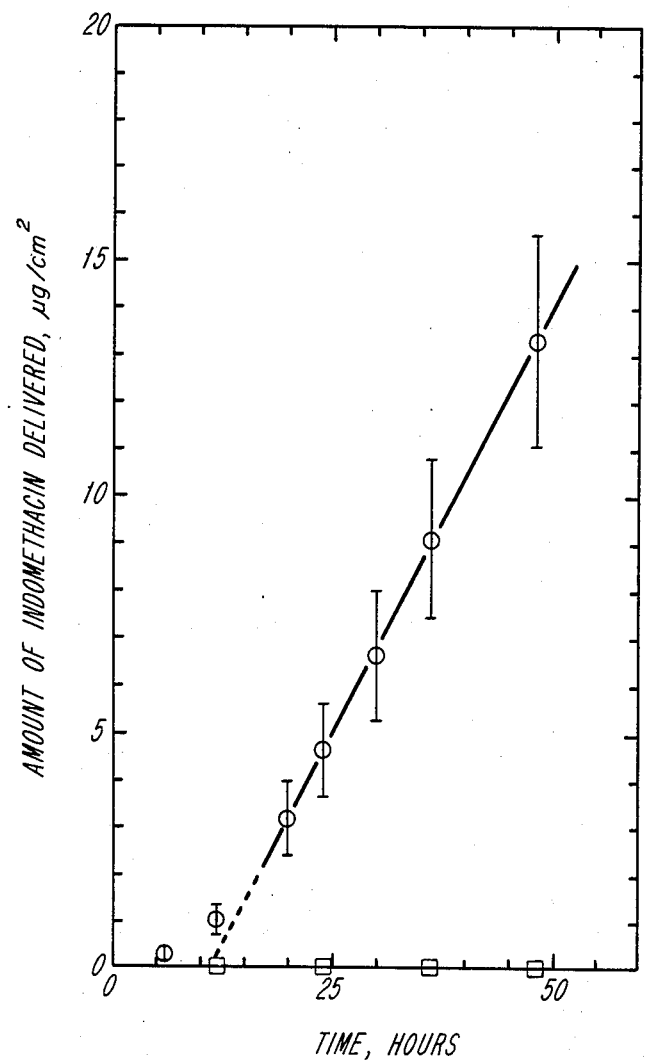
FIG. 3 graphically depicts the amount of indomethacin delivered over time.

In FIG. 3, the following legend should be applied:
(□) penetration from ointment of 1% w/w indomethacin without enhancer.
(○) penetration from ointment containing 8% w/w Deet; each experiment point represents the mean from 7 experiments in which skin was used. Bars indicate standard deviation.

The formulation which contained 8% Deet by weight was used to investigate regional variation in permeability of individual shed snake skin to both indomethacin and Deet. Since the tail and head regions had a different appearance from the rest of the skin, these were discarded before use, leaving approximately 70% of he whole dorsal area. Sections from the edge and central regions were selected and evaluated in the diffusion cell to examine the regional variation of individual shed snake skins.

The results from 6 snake skins are summarized in Table I below, in which the penetration of indomethacin has been expressed in terms of steady state flux and lag time. Unlike indomethacin, the penetration of Deet through the shed skin was so fast that its steady state flux could not be obtained. Instead, the amount of Deet which penetrated the shed snake skin for the first 6 hours was estimated (Table II below). Since the observed regional variation was found to be very small in every case for the indomethacin and Deet combination, a wide area of individual shed skin, at least 200 cm$^2$, were used for in vitro penetration studies described in the following examples.

TABLE I

In vitro indomethacin penetration of several shed snake skins from 1% w/w ointment containing 8% w/w Deet at 32° C.

| skin # | # of runs | Steady state flux, μg/cm²/hr. | Relative[1] premeability ratio | Lag time, hours |
|---|---|---|---|---|
| 1 | 4 | 0.294[2] ± 0.044[3] | 0.82 | 12.5[2] ± 0.4[3] |
| 2 | 4 | 0.397 ± 0.034 | 1.11 | 12.3 ± 1.9 |
| 3 | 5 | 0.436 ± 0.037 | 1.22 | 11.7 ± 1.3 |
| 4 | 4 | 0.367 ± 0.035 | 1.02 | 12.5 ± 0.3 |
| 5 | 7 | 0.360 ± 0.054 | 1.00 | 11.3 ± 1.2 |
| 6 | 7 | 0.298 ± 0.043 | 0.83 | 13.9 ± 2.5 |
|   |   | 0.359[4] ± 0.061[5] | 1.00 |   |

[1]This ratio was obtained by dividing the mean steady state flux of the individual snake skin by the mean steady state flux among 6 individual mean values.
[2]Mean value.
[3]Standard deviation.
[4]Mean value amount 6 individual mean values.
[5]Standard deviation of the 6 individual mean values.

TABLE II

Amount of Deet transferred across different snake skins from 1% w/w indomethacin ointments containing 8% w/w Deet at 32° C.

| Skin No.[1] | No. of Runs | Penetration of Deet for 6 hours, μg/cm² |
|---|---|---|
| 1 | 4 | 302[2](27[4]) ± 30[3] |
| 2 | 4 | 267 (24) ± 50 |
| 3 | 5 | 265 (23) ± 20 |
| 4 | 4 | 324 (29) ± 56 |

[1]These skin numbers correspond to those in Table I.
[2]Mean value.
[3]Standard deviation.
[4]Percent of applied amount.

EXAMPLE 2

Permeability of the snake skin was compared to that of the full thickness fuzzy rat skin using five different ointments containing 1% indomethacin by weight with (1) no enhancer; (2) 5% w/w Deet; (3) 10% w/w Deet; (4) 5% w/w Azone ®; 5% 2/2 Azone ®; (5) 10% w/w Azone ®. The comparison was not made in terms of steady state flux, but rather the amount of indomethacin which was transferred after 24 hours. This was done because the rapid decay of the living epidermis and dermis in the rat skin prevented meaningful measurements beyond 24 hours. This time limitation thus make it always difficult to obtain the steady state of flux of indomethacin through the rat skin.

As show in Table III below, indomethacin formulations containing an enhancer exhibited a marked increase in the rate of indomethacin penetration of the rat skin compared to its penetration from formulations without any enhancer. These results are in agreement with the snake skin studies. In fact, the t-test showed no statistically significant difference between the rat the snake skins with respect to all 4 formulations containing the enhancers (p>0.1).

The permeability of the rat and shed snake skins to the adjuvants themselves was also measured. The results, graphically shown in FIG. 4, suggest that Deet penetrates both skins at almost identical rates. Also, both skins showed a very low permeability to Azone ® (less than 0.5% of the total amount over a 24-hour period).

TABLE III

Comparison of amounts of indomethacin transferred across snake skin and fuzzy rat skin from 1% w/w indomethacin ointment with or without enhancer at 32° C.

| | Indomethacin transferred in 24 hours | | | |
|---|---|---|---|---|
| | Shed snake skin | | Fuzzy rat skin | |
| Formulation | n | amount of indomethacin, μg/cm² | n | amount of indomethacin, μg/cm² |
| No enhancer | 4 | not detected[3] | 3 | 0.8[1] ± 0.1[2] |
| 5% Deet | 3 | 2.7[1] ± 0.2[2] | 3 | 3.8 ± 2.0 |
| 10% Deet | 7 | 5.0 ± 0.6 | 7 | 3.9 ± 2.1 |
| 5% Azone ® | 6 | 7.2 ± 0.7 | 3 | 9.5 ± 4.0 |
| 10% Azone ® | 6 | 12.3 ± 1.2 | 7 | 11.8 ± 5.3 |

[1]Mean value.
[2]Standard deviation.
[3]Detection limit is 0.4 μg/cm².
n = number of runs.

Figure 4:
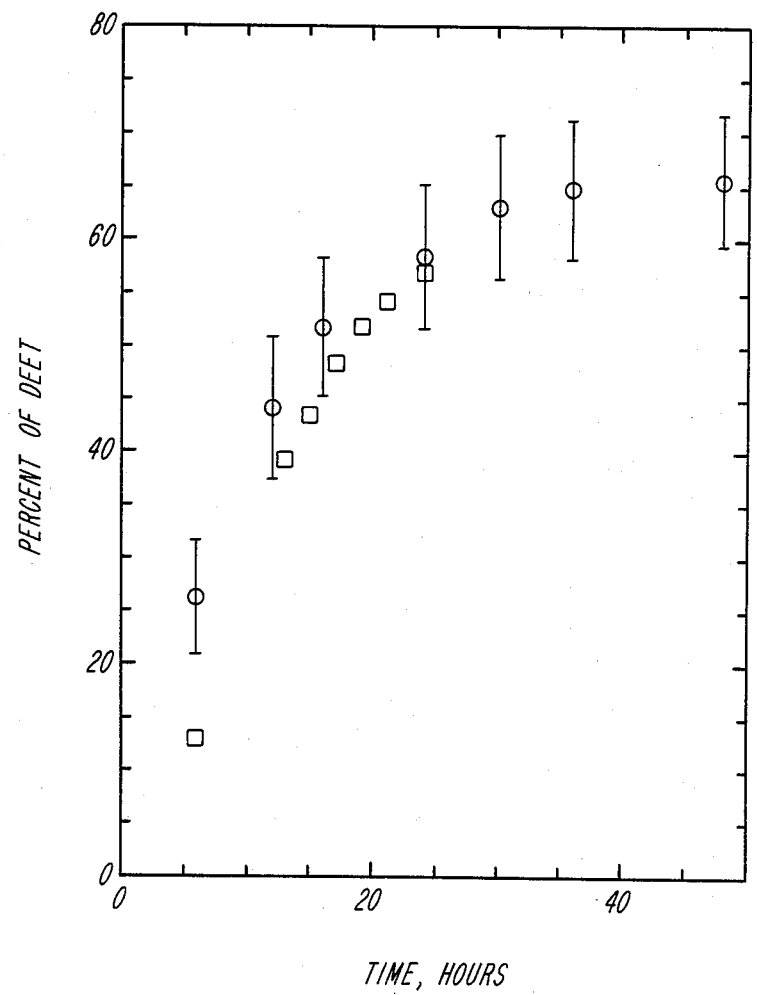
FIG. 4 graphically depicts Deet penetration of animal skins.

In viewing FIG. 4, the following legend should be applied:
( ○ )Snake skin. Each experimental point represents the mean from 5 experiments in which No. 3 skin was used (see Table II); bars indicate standard deviation.
(□) Fuzzy rat skin. Each experimental point represents the mean of 3 experiments.

These results strongly indicate that the shed snake skin can be used to predict the effect of dermal penetration of enhancers, particularly of the type studied in these experimental systems, and would be useful in predicting results of clinical behavior. Furthermore, because of the excellent reproducibility of the shed snake skin data the effect of enhancers could be evaluated with good accuracy, thus allowing studies of formulation and concentration dependency of various enhancers with much less effort than with either rat or cadaver skin.

Basically, therefore, it can be concluded from the foregoing experimental runs that diffusional measurements with snake skin as the barrier membrane in an in vitro system showed reproducibility substantially better than that found with fuzzy rat skin and that reported by others with cadaver skin. The use of a snake skin model barrier membrane appears to have significant advantages over those previously reported in that the skin shows much better reproducibility, convenient supply and excellent storage properties.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. In a system for testing the human skin penetration behavior of a bioactive agent comprising a model barrier membrane positioned between a donor formulation and a receptor solution, the improvement which comprises said model barrier membrane consisting essentially of shed snake skin.

2. The system of claim 1, wherein the shed snake skin is that of the black rat snake.

3. In an in vitro testing method for testing the ability of formulations to deliver bioactive agents across human skin, comprising the steps of
   (i) providing a dose of a donor formulation containing the bioactive agent to be followed, and a receptor solution,
   (ii) providing a barrier membrane to separate the donor formulation and the receptor solution, (iii) contacting the donor formulation with one side of the barrier membrane and the receptor solution with the other side of the barrier membrane for a time sufficient to produce penetration of the barrier membrane by the donor formulation, and, (iv) sampling the receptor solution and assaying same to determine the concentration of the bioactive agent in the receptor solution, the improvement wherein the model barrier membrane comprises shed snake skin.

4. The in vitro testing method of claim 3, wherein the shed snake skin of the barrier membrane is that of the black rat snake.

5. The in vitro testing method of claim 3, wherein the bioactive agent is indomethacin.

6. The in vitro testing method of claim 3, wherein the system in which the model barrier membrane is employed is a Franz Diffusion Cell.

7. The in vitro testing method of claim 3, wherein the formulation comprises enhancers for the delivery of the bioactive agent across human skin.

8. The in vitro testing method of claim 3, wherein the shed snake skin comprising the barrier membrane has been stored for at least one week prior to use.

9. The in vitro testing method of claim 3, wherein the shed snake skin comprising the barrier membrane had been stored for at least one month prior to use.

10. A method for testing the penetration behavior of a bioactive agent across human skin, comprising the steps of (i) providing a dose of a donor formulation containing the bioactive agent to be followed, and a receptor solution, (ii) providing a barrier membrane of shed snake skin to separate the donor formulation and the receptor solution, (iii) contacting the donor formulation with one side of the barrier membrane and the receptor solution with the other side of the barrier membrane for a time sufficient to produce penetration of the barrier membrane by the donor formulation, and (iv) sampling the receptor solution and assaying same to determine the concentration of the bioactive agent in the receptor solution.

11. The method of claim 10, wherein the shed snake skin of the barrier membrane is that of the black rat snake.

12. The method of claim 10, wherein the donor dose formulation comprises enhancers for the delivery of the bioactive agent across the human skin.

13. The method of claim 10, wherein the receptor solution is periodically sampled and assayed for the concentration of the bioactive agent.

14. The method of claim 10, wherein the bioactive agent is indomethacin.

15. The method of claim 10, wherein the shed snake skin of the barrier membrane had been stored at least one week prior to use.

16. The method of claim 10, wherein the shed snake skin of the barrier membrane had been stored at least one month prior to use.

* * * * *